(12) United States Patent
Knudsen et al.

(10) Patent No.: US 10,744,278 B2
(45) Date of Patent: Aug. 18, 2020

(54) INHALATION DEVICE

(71) Applicant: MICRODOSE THERAPEUTX, INC., Ewing, NJ (US)

(72) Inventors: Mark Knudsen, Stockton, NJ (US); Craig Oakum, Maple Shade, NJ (US); Kent Mosier, Tinton Falls, NJ (US); Henri Akouka, Mt. Laurel, NJ (US)

(73) Assignee: MICRODOSE THERAPEUTX, INC., Ewing, NJ (US)

( * ) Notice: Subject to any disclaimer, the term of this patent is extended or adjusted under 35 U.S.C. 154(b) by 708 days.

(21) Appl. No.: 15/324,478

(22) PCT Filed: Jul. 1, 2015

(86) PCT No.: PCT/US2015/038882
§ 371 (c)(1),
(2) Date: Jan. 6, 2017

(87) PCT Pub. No.: WO2016/007356
PCT Pub. Date: Jan. 14, 2016

(65) Prior Publication Data
US 2017/0197041 A1    Jul. 13, 2017

Related U.S. Application Data

(60) Provisional application No. 62/021,560, filed on Jul. 7, 2014.

(51) Int. Cl.
*A61M 11/00* (2006.01)
*A61M 15/00* (2006.01)
(Continued)

(52) U.S. Cl.
CPC ........ *A61M 11/005* (2013.01); *A61M 15/001* (2014.02); *A61M 15/0085* (2013.01);
(Continued)

(58) Field of Classification Search
CPC ............ A61M 11/005; A61M 15/0085; A61M 2207/00; A61M 2202/064;
(Continued)

(56) References Cited

U.S. PATENT DOCUMENTS

| | | | |
|---|---|---|---|
| 2,517,482 A | 8/1950 | Hall | 128/206 |
| 3,507,277 A | 4/1970 | Altounyan | 128/208 |

(Continued)

FOREIGN PATENT DOCUMENTS

| | | | |
|---|---|---|---|
| CN | 101489612 | 7/2009 | A61M 11/00 |
| CN | 101674858 | 3/2010 | A61M 15/00 |

(Continued)

OTHER PUBLICATIONS

Columbian Office Action (w/translation) issued in application No. NC2016/0005601, dated Dec. 28, 2016 (3 pgs).

(Continued)

*Primary Examiner* — Tu A Vo
(74) *Attorney, Agent, or Firm* — Hayes Soloway P.C.

(57) ABSTRACT

The disclosure describes an inhaler having a dosing chamber in which medicament is aerosolized with a vibrator piezoelectric transducer. A spacer is provided between a face of the transducer and a wall of the dosing chamber.

7 Claims, 2 Drawing Sheets

Tension Mechanism showing transducer, dose chamber, spacer and melinex tension ring

(51) Int. Cl.
 *B05B 17/06* (2006.01)
 *B05B 7/14* (2006.01)

(52) U.S. Cl.
 CPC .............. *B05B 7/14* (2013.01); *B05B 7/1413* (2013.01); *B05B 17/0661* (2013.01); *A61M 2202/04* (2013.01); *A61M 2202/064* (2013.01); *A61M 2207/00* (2013.01); *B05B 17/0607* (2013.01)

(58) Field of Classification Search
 CPC ............ A61M 2202/04; A61M 15/009; A61M 15/002; A61M 15/001; A61M 15/00; A61M 15/0001; A61M 15/0005; A61M 15/0086; A61M 11/00; A61M 11/08; B05B 7/14; B05B 7/1413; B05B 17/0661; B05B 17/0607
 See application file for complete search history.

(56) References Cited

U.S. PATENT DOCUMENTS

| | | | | |
|---|---|---|---|---|
| 3,518,992 | A | 7/1970 | Altounyan | 128/208 |
| 3,635,219 | A | 1/1972 | Altounyan et al. | 128/266 |
| 3,795,244 | A | 3/1974 | Lax et al. | 128/266 |
| 3,807,400 | A | 4/1974 | Cocozza | 128/266 |
| 3,831,606 | A | 8/1974 | Damani | 128/266 |
| 3,948,264 | A | 4/1976 | Wilke et al. | 128/266 |
| 4,976,259 | A * | 12/1990 | Higson | A61M 15/0085 128/200.14 |
| 5,458,135 | A | 10/1995 | Patton et al. | 128/200.14 |
| 5,694,920 | A | 12/1997 | Abrams et al. | 128/200.16 |
| 5,823,434 | A * | 10/1998 | Cooper | A61M 15/0086 239/102.2 |
| 6,026,809 | A | 2/2000 | Abrams et al. | 128/203.15 |
| 6,142,146 | A | 11/2000 | Abrams et al. | 128/203.15 |
| 6,152,130 | A | 11/2000 | Abrams et al. | 128/204.21 |
| 6,283,118 | B1 | 9/2001 | Lu | 128/200.16 |
| 6,328,033 | B1 * | 12/2001 | Avrahami | A61M 15/0085 128/200.25 |
| 7,080,644 | B2 | 7/2006 | Gumaste | 128/203.21 |
| 7,318,434 | B2 | 1/2008 | Gumaste et al. | 128/203.15 |
| 7,334,577 | B2 | 2/2008 | Gumaste et al. | 128/203.15 |
| 7,779,831 | B1 | 8/2010 | Von Hollen et al. | 128/200.16 |
| 7,779,837 | B2 | 8/2010 | Gumaste et al. | 128/203.15 |
| 7,810,495 | B2 | 10/2010 | Gumaste | 128/203.23 |
| 7,950,390 | B2 | 5/2011 | Gumaste | 128/203.21 |
| 8,196,576 | B2 | 6/2012 | Kriksunov et al. | 128/203.15 |
| 8,322,338 | B2 | 12/2012 | Gumaste et al. | 128/203.15 |
| 8,439,033 | B2 | 5/2013 | Gumaste et al. | 128/204.21 |
| 8,474,452 | B2 | 7/2013 | Gumaste et al. | 128/203.15 |
| 8,573,202 | B2 | 11/2013 | Gumaste | 128/203.12 |
| 8,371,294 | B2 | 12/2013 | Gumaste et al. | 128/200.24 |
| 2008/0202514 | A1 * | 8/2008 | Kriksunov | A61M 11/005 128/203.15 |
| 2011/0000481 | A1 | 1/2011 | Gumaste et al. | 128/200.23 |
| 2012/0285446 | A1 * | 11/2012 | Van Der Mark | A61M 11/005 128/200.14 |
| 2012/0291776 | A1 * | 11/2012 | Van Der Mark | A61M 11/005 128/200.14 |

FOREIGN PATENT DOCUMENTS

| | | | | |
|---|---|---|---|---|
| JP | 2007522880 | 8/2007 | | A61M 11/00 |
| JP | 2009530007 | 8/2009 | | A61M 13/00 |
| JP | 2010519973 | 6/2010 | | A61M 13/00 |
| JP | 2011072398 | 4/2011 | | A61M 11/00 |
| WO | WO2007028203 | 3/2007 | | A61M 11/00 |
| WO | WO2007107796 | 9/2007 | | A61M 15/00 |
| WO | WO2008106616 | 9/2008 | | A61M 16/00 |
| WO | WO2011085022 | 7/2011 | | A61M 15/00 |

OTHER PUBLICATIONS

International Preliminary Report on Patentability issued in application PCT/US2015/038882, dated Jan. 19, 2017 (8 pgs).
International Search Report issued in application No. PCT/US2015/038882, dated Sep. 8, 2015 (4 pgs).
Taiwanese Office Action (w/translation) issued in application No. 104122064, dated Dec. 5, 2016 (6 pgs).
Colombian Office Action (w/translation) issued in application No. NC2016/0005601, dated Feb. 23, 2018 (20 pgs).
Chinese Office Action (w/translation) issued in application No. 201580033300.2, dated Mar. 26, 2019 (13 pgs).
Australian Office Action issued in application No. 2015288166, dated May 9, 2019 (3 pgs).
European Office Action issued in application No. 15 738 226.8, dated Jul. 12, 2019 (6 pgs).
Japanese Office Action (w/translation) issued in application No. 2016-574383, dated May 27, 2019 (8 pgs).
Chilean Office Action (w/machine translation of relevant portions) issued in application No. 2017-000044, dated Jun. 6, 2018 (18 pgs).
Eurasian Office Action (w/translation) issued in application No. 201692173, dated Mar. 12, 2018 (2 pgs).
Ukraine Decision to Grant (w/translation) issued in application No. 2017 01042, dated Feb. 13, 2020 (9 pgs).
Ukraine Office Action (w/translation) issued in application No. 2017 01042, dated Dec. 10, 2019 (8 pgs).
Australian Notice of Acceptance issued in application No. 2015288166, dated Sep. 2, 2019 (3 pgs).
Chinese Office Action (w/ translation) issued in application No. 201580033300.2, dated Aug. 13, 2019 (10 pgs).
Japanese Decision to Grant (w/translation) issued in application No. 2016-57438, dated Oct. 24, 2019 (8 pgs).
Israeli Official Action (with relevant translated text) issued in application No. 249015, dated Jun. 10, 2020 (3 pgs).

* cited by examiner

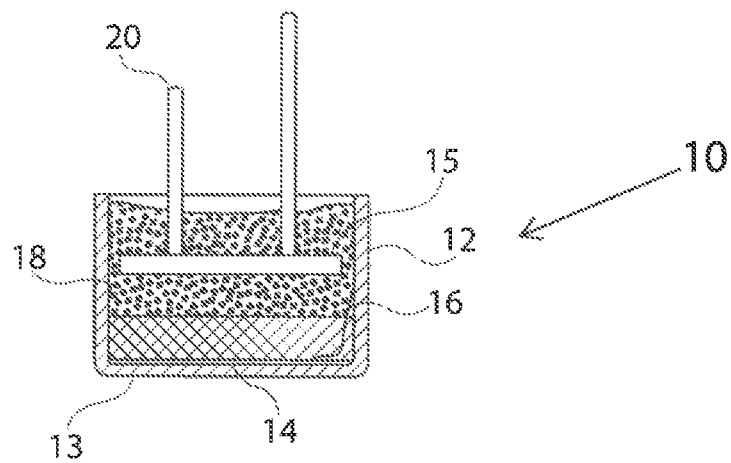
Figure 1. Piezo
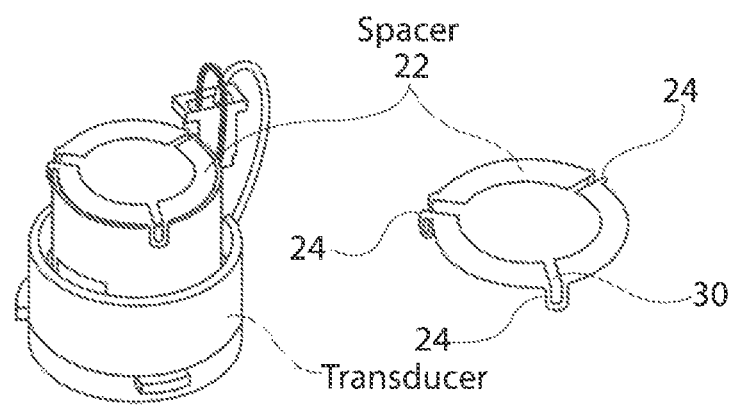
Figure 2: Piezo with spacer
Figure 3

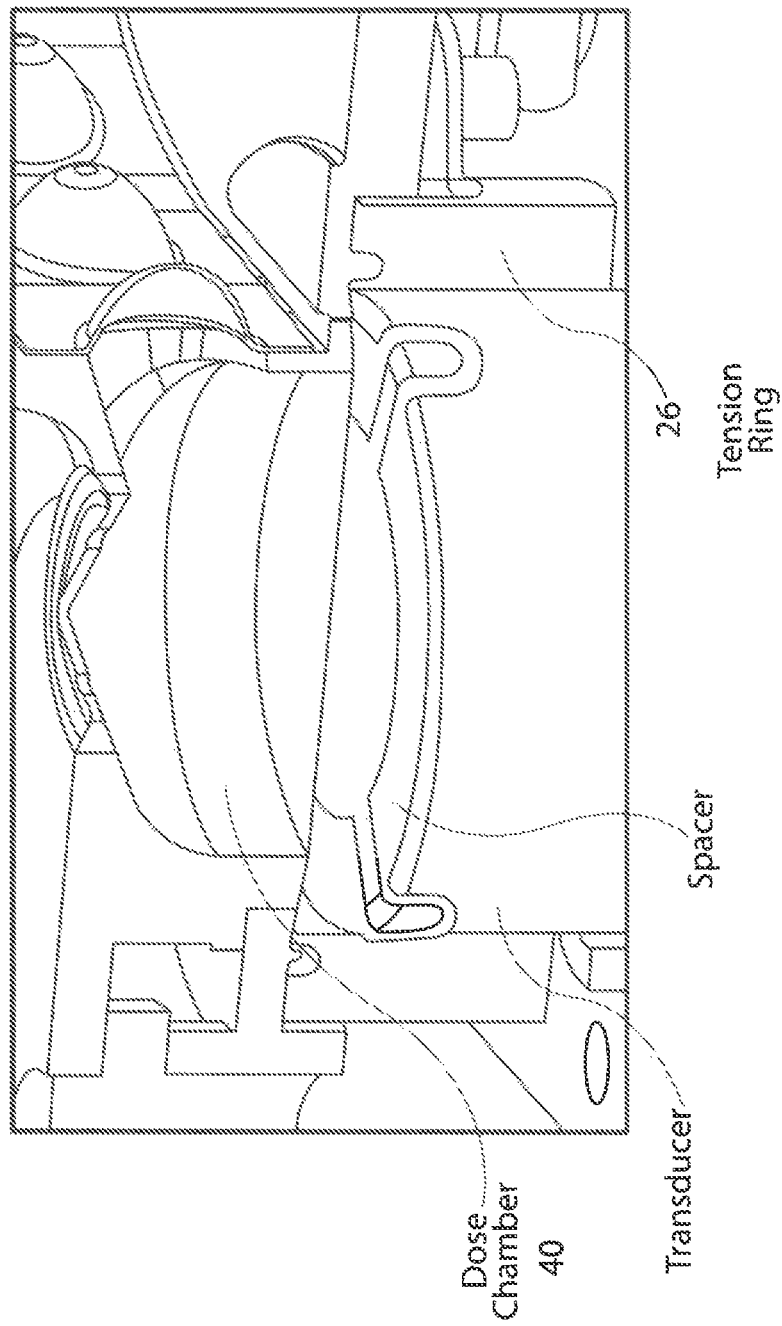
Figure 4: Tension Mechanism showing transducer, dose chamber, spacer and melinex tension ring

INHALATION DEVICE

The present invention relates generally to the field of inhalation devices, and more specifically, to inhalation devices that utilize vibration to facilitate suspension of particles of a medication into an inhaled gas stream (e.g., of inhaled air). The invention will be described in detail in connection with delivery of powdered medication to a patient, and will be described in connection with such utility, although other utilities, including specifically delivery of liquid droplets is contemplated.

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles may develop an electrostatic charge on themselves during manufacturing and storage. This may cause the particles to agglomerate or aggregate to themselves or formulation exceptients such as pulmonary grades of lactose, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms or less. For example, in the case of albuterol, a drug used in asthma, this is usually 25 to 50 micrograms. Current manufacturing equipment can effectively deliver aliquots of drugs in the milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) It is commonly held in the pharmaceutical industry that active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity air stream is used as the primary mechanism for breaking up the cluster of micronized particles or separating the drug particles from the carrier. Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages which are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medicament and potential variability of the delivered dose. Also, such prior art devices result in uncontrolled amounts or clumps, of powdered material being inhaled into the user's mouth, rather than a constant inhalation of controlled amounts of finely dispersed powder.

See also U.S. Pat. No. 3,948,264 to Wilke et al, who discloses a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon rotation puts one or more holes in the capsule so that upon vibration of the capsule by an electro-mechanical vibrator, the powdered drug may be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule.

The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through an outlet channel and concurrent pressing of a switch to activate the electromechanical vibrating means, air is sucked through inlet channels and the air stream through a secondary inlet channel raises the capsule up against a vibrating plunger rod. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) According to Wilke et al, the air stream through the inlet channels aids in withdrawal of powder from the capsule and carries this powder through the outlet channel to the mouth of the user. (Wilke et al, column 3, lines 45-55). Wilke et al further discloses that the electromechanical vibrator means may be placed at a right angle to the inlet chamber and that the amplitude and frequency of vibration may be altered to regulate dispensing characteristics of the inhaler.

Prior art devices such as above described have a number of disadvantages which makes them less than desirable for the delivery of dry powder to the lungs. Some of these disadvantages include:

The performance of the prior art inhalers depends on the flow rate generated by the user. Lower flow rate does not result in the powder being totally deaggregated and hence adversely affects the dose delivered to the patient.

inconsistency in the bioavailability of the drugs from dose-to-dose because of lack of consistency in the deaggregation process.

Large energy requirements for driving the electromechanical based inhalers which increases the size of the devices making them unsuitable for portable use.

Loss of medication from opened or topped capsules.

Deterioration of medication in open or topped capsule due to exposure to oxygen or moisture.

In prior U.S. Pat. Nos. 7,318,434 and 7,334,577 incorporated herein by reference, and assigned to the common assignee MicroDose Technologies, Inc., there are provided improvements over prior art inhalers that utilize vibration to facilitate suspension of power into an inhaled gas stream and which utilizes a synthetic jet to aerosolize drug powder from a blister pack or the like. As taught in the aforesaid U.S. Pat. Nos. 7,318,434 and 7,334,577 there are provided dry powder inhalers having a first chamber such as a blister pack or other container, for holding a dry powder, and a second chamber connected to the first chamber via a passageway for receiving an aerosolized form of the dry powder from the first chamber and for delivering the aerosolized dry powder to a user. A vibrator is coupled to the first chamber for aerosolizing the dry powder. The vibrator is energized and drives the powder from the chamber by synthetic jetting.

The medicament for dry powder inhalers is commonly contained in a blister pack or other flat bottom container that is placed in contact with the face of a piezoelectric transducer or vibrator, whereupon the vibration energy of the transducer is transferred to the medicament particles.

Accordingly, there exists a need to increase transducer displacement without increasing power or affecting its long-term reliability.

According the present invention there is provided an inhalation device having a dosing chamber for holding a pharmaceutical, and a vibrator for interacting with the chamber to aerosolize the pharmaceutical, in which an air space is provided between a face of the vibrator or transducer and a wall of the dosing chamber. The present inventors have surprisingly found that creating an air space between a face of the vibrator or transducer and a wall of the dosing chamber permits increased aerosol performance. Creating an air space between the face of the vibrator or transducer and a wall of the dosing chamber is against conventional wisdom which heretofore considered it necessary for the face of the vibrator or transducer to physically engage a wall of the dosing chamber in order to transfer a maximum acoustic energy to the dosing chamber. Unexpectedly, the resulting presently claimed structure exhibits increased performance.

In one aspect of the invention, the vibrator comprises a piezo transducer assembly.

In one embodiment a mechanical spacer element is provided between the face of the vibrator or transducer and a wall of the dosing chamber. Preferably, but not necessarily, the spacer comprises a metal ring that is clipped or fitted to the face of the vibrator or transducer.

Preferably, but not necessarily, the spacer is substantially circular in plan.

In one embodiment the spacer is positioned along at least a portion of an outer perimeter of the face of the vibrator or transducer.

In another embodiment, the spacer comprises a stand-off or spacer sleeve formed around and extending from the face end of the vibrator or transducer. In such embodiment, the stand-off sleeve preferably is formed of a polymeric material, more preferably a biaxially-oriented polyester film.

In another embodiment, the spacer is segmented with one or more gaps in the circular path.

In one embodiment the pharmaceutical comprises a dry powder.

In another embodiment of the invention, there is a method of arranging a vibrator or transducer in an inhaler device having a dosing chamber, comprising providing a spacer between a face of the vibrator or transducer and a wall of the dosing chamber, whereby to create an air space between the face of the vibrator or transducer and the surface of the dosing chamber.

In one embodiment of the method, the vibrator comprises a piezo transducer.

In one embodiment of the method, the spacer comprises a ring structure, preferably made of metal, on the face end of the vibrator or transducer.

In another embodiment of the method, the spacer preferably is substantially circular in plan.

In one embodiment of the method, the spacer comprises a stand-off sleeve affixed to the face end of the vibrator or transducer. In such embodiment the stand-off or spacer sleeve preferably is formed of a polymer film such as a biaxially-oriented polyester film.

In yet another embodiment of the method, the pharmaceutical comprises a dry powder.

Further features and advantages of the present invention will be seen from the following detailed description, taken in conjunction with the accompanying drawings, wherein:

FIG. 1 is a cross-sectional view of a piezoelectric actuator made in accordance with the present invention;

FIG. 2 is a perspective view of a vibrator or transducer with a spacer element in accordance with the present invention;

FIG. 3 is a perspective view showing details of a spacer element in accordance with the present invention; and FIG. 4 is a perspective view, partially in cross-section, showing a tension mechanism, transducer, a dose chamber, a spacer sleeve and a tension ring in accordance with the present invention.

As used herein the term "dosing chamber" is intended to comprise a blister pack in which a pharmaceutical is held, for aerosolization and delivery to a patient as described, for example, in U.S. Pat. Nos. 5,694,920; 6,026,809; 6,142,146; 6,152,130; 7,334,577; 7,080,644; 7,810,495; 7,950,390; 8,322,338; 8,573,202; 7,318,434; 7,779,837; 8,474,452; 8,439,033 and U.S. Published Application 2011/0000481, the contents of which are incorporated herein by reference. The "dosing chamber" also may comprise a dosing chamber into which a controlled quantity of a pharmaceutical is introduced for aerosolization and delivery to a patient or a combined reservoir and dosing chamber configured to contain multiple doses of a pharmaceutical material as described, for example in PCT Application PCT/US2011/020252, the contents of which are incorporated herein by reference.

As used herein, a pharmaceutical may comprise a dry powder pharmaceutical or a liquid pharmaceutical.

The terms "vibrator, transducer and piezo" are all used interchangeably throughout this application.

Referring to FIGS. 1-4 of the drawings, a vibrator or transducer assembly 10 in accordance with the present invention comprises a rigid cylindrical case 12 formed of, for example aluminum, that is closed at one end by a wall 13. A piezoelectric ceramic disc 14 is located within cylinder 12 on wall 13. A positive lead wire 16 is affixed to the inside surface of the piezoelectric disc 14 and a circuit board 15. Disc 14 is adhered to an interior surface of wall 13 using a silicone adhesive 18 to provide strain relief and an environmental seal. A negative lead line 20 is also attached to the circuit board 15, which in turn is encased or potted within a silicone adhesive 18.

Although this configuration protects the piezo from external contamination, the bond between the ceramic piezo and the metal housing limits the amount of mechanical displacement that is possible. This places a restriction on the performance of the aerosol generator. It would be highly desirable to remove this restriction. The challenge is to provide more displacement to aerosolize the medication via synthetic jetting from a dosing chamber, without stressing the bond or the piezo, potentially damaging both. Thus, it is desirable to increase the resultant effect of the displacement of the piezo without compromising the overall robustness of the design.

It was discovered that providing a small, essentially closed air space between a face of the vibrator or transducer and a wall of the dosing chamber 40, substantially increases performance. This was achieved by placing a small metal spacer 22 as shown in FIGS. 2-3, over the face of the vibrator or transducer assembly. The spacer creates an air gap between the transducer face and bottom membrane of the dosing chamber. It is believed that the interaction between the air gap and the film can cause the film to vibrate with a combination of modes. One mode resembles that of the transducer: a simple drum skin mode. Relative motion of the transducer and film in this mode compresses and expands the air, so that it acts like an axial spring. The other mode resembles a "ripple"; it has several wavelengths across the diameter of the film and can occur at a much larger amplitude than the drum skin mode. These ripples may be conducive to fluidizing the powder and increasing performance both in terms of how quickly jetting is established and the rate and extent of exiting the formulation from the dosing chamber.

Referring in particular to FIG. 3, the spacer 22 comprises a generally flat disc having a plurality (preferably 3) of downwardly extending tabs 24 which are friction fitted over the wall 18 of the aluminum case 12. Tabs 24 also may be adhered to the case 12, e.g. using an adhesive or solder. Spacer 22 preferably is round, and has one or more gaps 30 in its circular path.

Alternatively, as shown in FIG. 4 in order to further increase the air space and better stabilize the spacer 22, a tension and stand-off ring 26 may be fitted around the outer periphery of the aluminum case 12. Ring 26 preferably is formed of a resiliently deformable material, preferably a polymer material, more preferably a biaxially-oriented polyester material. In a preferred embodiment ring 26 is formed of a biaxially-oriented polyester film such as Melinex®, which is available from Tekra, a division of EIS, Inc. of New Berlin, Wis. Ring 26 serves the multiple purposes of stabilizing and holding spacer 22 to the aluminum case 12, increasing the size of the air gap between the face of the vibrator or transducer and a wall of the dosing chamber, and sealing the vibrator or transducer to the wall of the dosing chamber.

The drive circuit for driving the vibrator or transducer in accordance with the present invention may comprise a conventional transducer drive circuit. For example, the drive circuit that is used may comprise a drive circuit as described in our aforesaid U.S. patent application Ser. No. 12/392,686, the contents of which are incorporated herein by reference.

For example, as described in our aforesaid U.S. patent application Ser. No. 12/392,686, the transducer receives power from power supply 10. Field effect transistors comprise an electronic switch that is opened and closed at the primary resonance frequency of the transducer. Alternatively, the drive circuit may be constructed with a single transistor. An inductor stores energy when the electronic switch is closed. When the electronic switch is open, all of the energy in the inductor is transferred to the transducer. A diode effectively disconnects the inductor from the transducer after the energy of the inductor has been transferred to the transducer, thereby insuring the maximum energy transfer during a cycle.

Other waveforms may also be used. The primary requirement is that the drive waveform produces sufficient harmonic energy such that a secondary resonant frequency of the piezoelectric transducer is excited whereby a mechanical oscillation at the secondary resonance occurs. It also is possible to generate a waveform comprising two sinusoidal signals at two different frequencies corresponding to the primary and a secondary resonance frequency of the transducer. Any signal that has sufficient energy at both the primary and a secondary resonance frequency such that significant mechanical motion of the transducer face is created at both frequencies creates the motion of the piezoelectric transducer face that has the desired effect.

In an embodiment of the present invention, the dry powder pharmaceutical may comprise an active pharmaceutical ingredient, optionally further comprising a carrier. The carrier may be lactose.

In an embodiment, the active pharmaceutical ingredient may be an antiviral compound; a bronchodilator, optionally selected from a long acting muscarinic antagonist (LAMA) or a long-acting beta$_2$-agonist (LABA); and/or a corticosteroid.

Examples of appropriate antiviral compounds include MDT-637, ribavirin, palivizumab, RSV-IGIV, ALN-RSV01, BMS-433771, RFI-641, RSV604, BTA9881, TMC-353121, MBX-300, YM-53403, RV568, a RSV-F Particle Vaccine, and derivatives or pharmaceutically acceptable salts thereof.

Examples of appropriate LAMAs include glycopyrronium, dexpirronium, tiotropium, oxybutynin, ipratropium, darifenacin, and derivatives or pharmaceutically acceptable salts thereof.

Examples of appropriate LABAs include formoterol, salmeterol, indacaterol, olodaterol, bambuterol, and derivatives or pharmaceutically acceptable salts thereof.

Examples of appropriate corticosteroids include budesonide, fluticasone, beclomethasone, flunisolide, triamcinolone, ciclesonide, loteprednol, fluorometholone, and derivatives or pharmaceutically acceptable salts thereof.

In a further aspect, the invention comprises an inhaler of the first aspect for use in treating a respiratory disease.

In an embodiment, the respiratory disease is selected from chronic obstructive pulmonary disease (COPD), asthma, acute bronchitis, acute respiratory distress syndrome (ARDS), emphysema, chronic bronchitis and respiratory syncytial virus.

It should be emphasized that the above-described embodiments of the present device and process, particularly, and "preferred" embodiments, are merely possible examples of implementations and merely set forth for a clear understanding of the principles of the invention. Many different embodiments of the invention described herein may be designed and/or fabricated without departing from the spirit and scope of the invention. For example, by placing a stand-off sleeve over the end of the transducer assembly, the metal spacer on the face of the vibrator or transducer assembly may be eliminated. Alternatively, the spacer element may be an integral part of the transducer assembly. All these and other such modifications and variations are intended to be included herein within the scope of this disclosure and protected by the following claims. Therefore the scope of the invention is not intended to be limited except as indicated in the appended claims.

The invention claimed is:

1. An inhalation device comprising a dosing chamber configured for holding a dry powder pharmaceutical, and a vibrator for interaction with the dosing chamber to aerosolize the pharmaceutical, the inhalation device comprising:
  a spacer comprising an inner surface and an outer surface, the inner surface forms a through-hole in a center portion of the spacer, wherein the spacer is substantially circular in plan, the spacer is located around a perimeter of a face of the vibrator between the face of the vibrator and a bottom wall of the dosing chamber such that an air space is created by the through-hole in the center portion between the inner surface, the face of the vibrator and the bottom wall of the dosing chamber, wherein the spacer is a metal plate, and comprises a plurality of tabs that are coupled to a side of the vibrator, and wherein a stand-off sleeve is placed over the spacer and the vibrator to increase the air space and to stabilize the spacer.

2. The device of claim 1, wherein the vibrator comprises a piezo transducer assembly.

3. The device of claim 1, wherein the stand-off sleeve is formed of a biaxially-oriented polymer material.

4. The device of claim 1, wherein the spacer is segmented with one or more gaps.

5. A method for arranging a vibrator in a dry powder inhaler device, having a dosing chamber configured to hold the dry powder, said method comprising:
  positioning a spacer having an inner surface and an outer surface, the inner surface forms a through-hole in a center portion of the spacer, wherein the spacer is substantially circular in plan, around a perimeter of a face of the vibrator between the face of the vibrator and a bottom wall of the dosing chamber, wherein an air space is created by the through-hole in the center portion between the inner surface, the face of the vibrator and the bottom wall of the dosing chamber, wherein the spacer is a metal plate, and comprises a plurality of tabs that are coupled to a side of the vibrator, and wherein a stand-off sleeve is placed over the spacer and the vibrator to increase the air space and to stabilize the spacer.

6. The method of claim 5, wherein the vibrator comprises a piezo transducer.

7. The method of claim 5, wherein the stand-off sleeve is formed of a polymer material.

* * * * *